(12) United States Patent
Hagiya et al.

(10) Patent No.: US 8,299,264 B2
(45) Date of Patent: Oct. 30, 2012

(54) METHOD FOR PRODUCING OXADIAZOLINONE COMPOUND AND INTERMEDIATE THEREOF

(75) Inventors: Koji Hagiya, Ibaraki (JP); Yasutaka Aoyagi, Oita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 52 days.

(21) Appl. No.: 13/124,416

(22) PCT Filed: Oct. 19, 2009

(86) PCT No.: PCT/JP2009/068296
§ 371 (c)(1),
(2), (4) Date: Apr. 15, 2011

(87) PCT Pub. No.: WO2010/047400
PCT Pub. Date: Apr. 29, 2010

(65) Prior Publication Data
US 2011/0207936 A1    Aug. 25, 2011

(30) Foreign Application Priority Data

Oct. 20, 2008 (JP) .................................. 2008-269413

(51) Int. Cl.
*C07D 271/113* (2006.01)
*C07C 271/58* (2006.01)
*C07C 269/04* (2006.01)

(52) U.S. Cl. .......................................... 548/144; 560/25

(58) Field of Classification Search .................. 548/144; 560/25
See application file for complete search history.

(56) References Cited

U.S. PATENT DOCUMENTS 4,150,142 A * 4/1979 Boesch .......................... 514/364

FOREIGN PATENT DOCUMENTS

| JP | 51-101981 A | 9/1976 |
| JP | 57-50950 A | 3/1982 |
| JP | 60-19302 B2 | 5/1985 |

OTHER PUBLICATIONS

International Search Report, dated Nov. 24, 2009, issued in PCT/JP2009/068296.
English translation of International Preliminary Report on Patentability and Written Opinion of the International Searching Authority, dated May 17, 2011, for International Application No. PCT/JP2009/068296.

* cited by examiner

*Primary Examiner* — Yong Chu
(74) *Attorney, Agent, or Firm* — Birch, Stewart, Kolasch & Birch, LLP

(57) ABSTRACT

A compound represented by the formula (1):

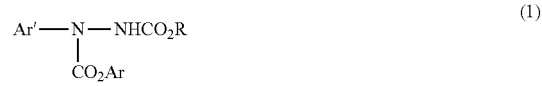

wherein Ar represents an aromatic hydrocarbon group having 6 to 20 carbon atoms which may have a substituent, Ar' represents an aromatic hydrocarbon group having 6 to 20 carbon atoms which may have a substituent, and R represents an alkyl group having 1 to 4 carbon atoms.

9 Claims, No Drawings

METHOD FOR PRODUCING OXADIAZOLINONE COMPOUND AND INTERMEDIATE THEREOF

TECHNICAL FIELD

The present invention relates to a method for producing an oxadiazolinone compound and an intermediate thereof.

BACKGROUND ART

As a method for producing an oxadiazolinone compound, there is known a method in which a 2-aryl-substituted hydrazinecarboxylic acid methyl ester is treated with phosgene to give a 2-(chlorocarbonyl)-2-aryl-substituted hydrazinecarboxylic acid methyl ester, which is then cyclized by the action of a base (for example, refer to JP-B-60-19302). However, such a method uses phosgene having strong toxicity, which requires facilities provided with safety measures for industrial practice.

DISCLOSURE OF THE INVENTION

Thus, the present inventors have developed a method for producing an oxadiazolinone compound without using phosgene having strong toxicity, thus accomplishing the present invention.

That is, the present application provides the following inventions.

[1] A compound represented by the formula (1):

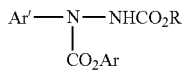 (1)

wherein Ar and Ar' each independently represents an aromatic hydrocarbon group having 6 to 20 carbon atoms which may have a substituent, and R represents an alkyl group having 1 to 4 carbon atoms.

[2] The compound according to [1], wherein Ar is a phenyl group, and Ar' is a phenyl group which has an alkoxy group having 1 to 4 carbon atoms.

[3] The compound according to [1], wherein Ar is a phenyl group, Ar' is a 2-methoxyphenyl group, and R is a methyl group.

[4] A method for producing an oxadiazolinone compound represented by the formula (2):

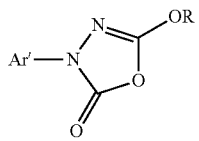 (2)

wherein Ar' and R have the same meanings as defined below, which comprises step I of reacting a compound represented by the formula (3):

 (3)

wherein Ar' represents an aromatic hydrocarbon group having 6 to 20 carbon atoms which may have a substituent, and R represents an alkyl group having 1 to 4 carbon atoms, with a compound represented by the formula (4):

$$ClCO_2Ar \quad (4)$$

wherein Ar represents an aromatic hydrocarbon group having 6 to 20 carbon atoms which may have a substituent; and step II of reacting a compound represented by the formula (1):

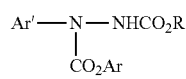 (1)

wherein Ar and Ar' each independently has the same meaning as defined above, which is obtained by step I, with a strong base.

[5] A method for producing an oxadiazolinone compound represented by the formula (2):

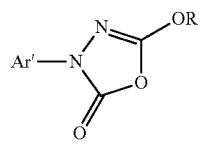 (2)

wherein Ar' and R have the same meanings as defined below, which comprises a step of reacting a compound represented by the formula (1):

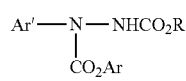 (1)

wherein Ar and Ar' each independently represent an aromatic hydrocarbon group having 6 to 20 carbon atoms which may have a substituent, and R represents an alkyl group having 1 to 4 carbon atoms, with a strong base.

[6] The method according to [4] or [5], wherein the strong base is selected from the group consisting of an alkali metal hydride, an alkali metal amide compound, and an alkali metal hydroxide.

[7] A method for producing a compound represented by the formula (1):

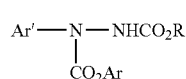 (1)

wherein Ar, Ar' and R have the same meanings as defined below, which comprises a step of reacting a compound represented by the formula (3):

 (3)

wherein Ar' represents an aromatic hydrocarbon group having 6 to 20 carbon atoms which may have a substituent, and R represents an alkyl group having 1 to 4 carbon atoms, with a compound represented by the formula (4):

wherein Ar represents an aromatic hydrocarbon group having 6 to 20 carbon atoms which may have a substituent.
[8] The method according to [4], [5] or [7], wherein Ar is a phenyl group, and Ar' is a phenyl group which has an alkoxy group having 1 to 4 carbon atoms.
[9] The method according to [4], [5] or [7], wherein Ar is a phenyl group, Ar' is a 2-methoxyphenyl group, and R is a methyl group.

EFFECTS OF THE INVENTION

According to the present invention, it is possible to produce an oxadiazolinone compound industrially easily without requiring special facilities since phosgene having strong toxicity is not used.

BEST MODE FOR CARRYING OUT THE INVENTION

Hereinafter, the present invention will be described in detail.

The compound of the present invention (hereinafter, this compound is sometimes referred to as a "compound (1)") is represented by the following formula (1).

In the present description, Ar represents an aromatic hydrocarbon group having 6 to 20 carbon atoms which may have a substituent.

In the present description, examples of the aromatic hydrocarbon group include a phenyl group and a naphthyl group.

Examples of the substituent in the aromatic hydrocarbon group include alkyl groups having 1 to 6 carbon atoms, such as a methyl group, an ethyl group, a propyl group, an isopropyl group, a butyl group, an isobutyl group, a sec-butyl group, a tert-butyl group, a pentyl group, and a hexyl group; haloalkyl groups having 1 to 6 carbon atoms, such as a fluoromethyl group and a trifluoromethyl group; alkoxy-substituted alkyl groups having 1 to 10 carbon atoms, such as a methoxymethyl group, an ethoxymethyl group, and a methoxyethyl group; alkoxy groups having 1 to 6 carbon atoms, such as a methoxy group, an ethoxy group, a propoxy group, an isopropoxy group, a butoxy group, an isobutoxy group, a sec-butoxy group, a tert-butoxy group, and a pentyloxy group; haloalkoxy groups having 1 to 6 carbon atoms, such as a fluoromethoxy group and a trifluoromethoxy group; alkoxy-substituted alkoxy groups having 2 to 10 carbon atoms, such as a methoxymethoxy group, an ethoxymethoxy group, and a methoxyethoxy group; halogen atoms such as a fluorine atom and a chlorine atom; a nitro group; cycloalkyl groups having 3 to 6 carbon atoms, such as a cyclopentyl group; and cycloalkyloxy groups such as a cyclopentyloxy group.

Specific examples of Ar include a phenyl group, an alkyl-substituted phenyl group, a halogen-substituted phenyl group, and an alkoxy-substituted phenyl group, and more specific examples thereof include a 2-methylphenyl group, a 4-chlorophenyl group, a 4-methylphenyl group, and a 2-methoxyphenyl group.

In the present description, Ar' represents an aromatic hydrocarbon group having 6 to 20 carbon atoms which may have a substituent.

Specific examples of Ar' include a phenyl group, an alkyl-substituted phenyl group, a halogen-substituted phenyl group, and an alkoxy-substituted phenyl group, and more specific examples thereof include a 2-methylphenyl group, a 4-chlorophenyl group, a 4-bromophenyl group, and a 2-methoxyphenyl group.

In the present description, R represents an alkyl group having 1 to 4 carbon atoms.

Examples of the alkyl group represented by R include a methyl group, an ethyl group, a n-propyl group, an isopropyl group, a n-butyl group, and a t-butyl group.

As described above, the compound (1) has a structure represented by the formula (1) and therefore it can be easily converted into a compound (2). Accordingly, the compound (1) is useful as an intermediate in the production of the compound (2).

The compound (1) is preferably a compound of the formula (1) in which Ar is a phenyl group, and Ar' is a phenyl group which has an alkoxy group having 1 to 4 carbon atoms, and more preferably a compound of the formula (1) in which Ar is a phenyl group, Ar' is a 2-methoxyphenyl group, and R is a methyl group.

Examples of the compound (1) include 1-methoxycarbonyl-2-phenoxycarbonyl-2-(2-methoxyphenyl) hydrazine, 1-methoxycarbonyl-2-(4-nitrophenoxycarbonyl)-2-(2-methoxyphenyl) hydrazine, 1-methoxycarbonyl-2-(4-chlorophenoxycarbonyl)-2-(2-methoxyphenyl) hydrazine, 1-(2-fluorophenoxycarbonyl)-1-(2-methoxyphenyl)-2-methoxycarbonylhydrazine, 1-methoxycarbonyl-2-(4-methylphenoxycarbonyl)-2-(2-methoxyphenyl) hydrazine, 1-methoxycarbonyl-2-(2-methoxyphenoxycarbonyl)-2-(2-methoxyphenyl) hydrazine, 1-methoxycarbonyl-2-(4-trifluoromethylphenoxycarbonyl)-2-(2-methoxyphenyl) hydrazine, 1-methoxycarbonyl-2-(phenoxycarbonyl)-2-(4-methylphenyl) hydrazine, 1-methoxycarbonyl-2-(phenoxycarbonyl)-2-(4-chlorophenyl) hydrazine, 1-methoxycarbonyl-2-(phenoxycarbonyl)-2-(4-chlorophenyl) hydrazine, 1-methoxycarbonyl-2-(phenoxycarbonyl)-2-(2-fluorophenyl) hydrazine, 1-methoxycarbonyl-2-(phenoxycarbonyl)-2-(4-bromophenyl) hydrazine, 1-methoxycarbonyl-2-(phenoxycarbonyl)-2-(4-nitrophenyl) hydrazine, 1-ethoxycarbonyl-2-phenoxycarbonyl-2-phenylhydrazine, 1-ethoxycarbonyl-2-(phenoxycarbonyl)-2-(2-methoxyphenyl) hydrazine, 1-(phenoxycarbonyl)-1-(2-methoxyphenyl)-2-propoxycarbonylhydrazine, 1-methoxycarbonyl-2-(phenoxycarbonyl)-2-phenylhydrazine, 1-(4-chlorophenoxycarbonyl)-1-phenyl-2-methoxycarbonylhydrazine, 1-butoxycarbonyl-2-(2-fluorophenoxycarbonyl)-2-(2-methoxyphenyl) hydrazine, and 1-butoxycarbonyl-2-phenoxycarbonyl-2-(2-methoxyphenyl) hydrazine.

The compound (1) can be produced by an operation of step I described hereinafter.

The method for producing an oxadiazolinone compound of the present invention include step I of reacting a compound represented by the formula (3) (hereinafter sometimes referred to as a compound (3)) with a compound represented by the formula (4) (hereinafter sometimes referred to as a compound (4)) and step II of reacting the compound (1) obtained by step I with a strong base.

The method for producing the compound (1) including step I, and the method for producing the oxadiazolinone compound (hereinafter sometimes referred to as a compound (2)) including step II are also one of the present invention.

In the present description, a compound (3) is represented by the formula (3):

(3)

wherein Ar' and R are as respectively defined above.

Examples of the compound (3) include 1-(C1-C4 alkoxy)carbonyl-2-phenylhydrazine, 1-(C1-C4 alkoxy)carbonyl-2-[(C1-C4 alkoxy)phenyl] hydrazine, and 1-(C1-C4 alkoxy)carbonyl-2-halophenylhydrazine, and more specific examples thereof include 1-methoxycarbonyl-2-phenylhydrazine, 1-ethoxycarbonyl-2-phenylhydrazine, 1-methoxycarbonyl-2-(2-methoxyphenyl) hydrazine, 1-methoxycarbonyl-2-(4-methylphenyl) hydrazine, 1-methoxycarbonyl-2-(4-chlorophenyl) hydrazine, 1-ethoxycarbonyl-2-(4-methoxyphenyl) hydrazine, 1-methoxycarbonyl-2-(2-fluorophenyl) hydrazine, 1-methoxycarbonyl-2-(4-nitrophenyl) hydrazine, 1-ethoxycarbonyl-2-(2-methoxyphenyl) hydrazine, 1-(2-methoxyphenyl)-2-propoxycarbonylhydrazine, and 1-butoxycarbonyl-2-(2-methoxyphenyl) hydrazine.

As the compound (3), a commercially available product may be used, or those produced by the method described in JP-B-60-19302 or the like, that is, a method of reacting phenylhydrazine with a compound represented by ClCO$_2$R may be used.

In the present description, the compound (4) is represented by the formula (4):

(4)

wherein Ar is as defined above.

Examples of the compound (4) include phenyl chloroformate, (nitro-substituted phenyl)chloroformate, (halogen-substituted phenyl)chloroformate, (C1-C4 alkyl-substituted phenyl)chloroformate, (C1-C4 alkoxy-substituted phenyl) chloroformate, and (C1-C4 haloalkyl-substituted phenyl) chloroformate, and more specific examples thereof include phenyl chloroformate, (4-nitrophenyl)chloroformate, (4-chlorophenyl)chloroformate, (2-fluorophenyl)chloroformate, (4-methylphenyl) chloroformate, (2-methoxyphenyl) chloroformate, and (4-trifluoromethylphenyl)chloroformate.

As the compound (4), a commercially available product may be used, or those produced by a known method described in Tetrahedron, 58, 10011 (2002) or the like may be used.

In step I, the use amount of the compound (4) may be 1 mol or more, usually from 1 to 10 mol, and preferably from 1 to 3 mol, per mol of the compound (3).

In the reaction of step I, it is preferred to optionally use a base. It is possible to neutralize hydrogen chloride produced as a by-product in the reaction by using the base.

Any of an organic base and an inorganic base can be used as such a base.

Examples of the organic base include tertiary amines such as triethylamine, trioctylamine, and diisopropylethylamine; nitrogen-containing aromatic compounds such as pyridine and imidazole; and alkali metal alkoxides such as sodium methoxide and sodium ethoxide.

Examples of the inorganic base include carbonates of alkali metals or alkali earth metals, such as lithium carbonate, sodium carbonate, potassium carbonate, cesium carbonate, magnesium carbonate, and calcium carbonate; hydrogen carbonates of alkali metals or alkali earth metals, such as lithium hydrogencarbonate, sodium hydrogencarbonate, potassium hydrogencarbonate, cesium hydrogencarbonate, magnesium hydrogencarbonate, and calcium hydrogencarbonate; hydroxides of alkali metals or alkali earth metals, such as lithium hydroxide, sodium hydroxide, potassium hydroxide, cesium hydroxide, magnesium hydroxide, and calcium hydroxide; and any mixtures thereof. Carbonates of alkali metals or alkali earth metals are preferred.

The use amount of the base may be 1 mol or more per mol of the compound (4), which is usually within the range from 1 to 3 mol although there is no particular upper limit.

The reaction of step T is usually carried out in the presence of an organic solvent. Examples of the organic solvent include ether solvents such as methyl tert-butyl ether, tetrahydrofuran, dimethoxyethane, and diglyme; nitrile solvents such as acetonitrile and propionitrile; and aromatic hydrocarbon solvents such as toluene and xylene.

There is no particular limitation on the use amount of the organic solvent. Taking volume efficiency into consideration, the use amount of the organic solvent is usually 0.5 parts by weight or more and 100 parts by weight or less per part by weight of the compound (3), from the viewpoint of practical use.

The reaction temperature is usually within the range from −20 to 200° C., and preferably from 0 to 100° C.

In the reaction of step I, it is preferred that the compound (3), an organic solvent and, if necessary, a base are mixed in any order and a compound (4) is added to the obtained mixture.

The reaction is usually carried out under a normal pressure condition. Proceeding of the reaction can be confirmed by conventional analysis means such as gas chromatography, high-performance liquid chromatography, thin-layer chromatography, NMR, and IR.

After completion of the reaction, the compound (1) can be isolated from the mixture by means such as crystallization, filtration, distillation, and extraction. The isolated compound (1) may be further purified, for example, by conventional purification means such as rectification and column chromatography.

Next, step II of reacting the compound (1) with a strong base will be described.

Examples of the strong base include alkali metal hydrides such as lithium hydride, sodium hydride, and potassium hydride; alkali metal amide compounds such as lithium amide, sodium amide, and potassium amide; and alkali metal hydroxides such as lithium hydroxide, sodium hydroxide, and potassium hydroxide. Alkali metal hydrides and alkali metal hydroxides are preferable, and sodium hydride and potassium hydroxide are more preferable.

The use amount of the strong base may be usually 0.8 mol or more per mol of the compound (1), which is preferably within the range from 0.8 to 3 mol although there is no particular upper limit.

The reaction of step II is usually carried out in the presence of an organic solvent. Examples of the organic solvent include ether solvents such as methyl tert-butyl ether, tetrahydrofuran, dimethoxyethane, and diglyme; nitrile solvents such as acetonitrile and propionitrile; and aromatic hydrocarbon solvents such as toluene and xylene. There is no particular limitation on the use amount of the organic solvent. Taking volume efficiency into consideration, the use amount of the organic solvent is usually 0.5 parts by weight or more and 100 parts by weight or less per part by weight of the compound (1), from the viewpoint of practical use.

The reaction temperature is usually within the range from −20 to 100° C., and preferably from −20 to 50° C.

In the reaction of step II, the compound (1) and an organic solvent may be mixed and a strong base may be added to the obtained mixture, or a strong base and an organic solvent may be mixed and the compound (1) may be added to the obtained mixture, or the compound (1) and a strong base may be simultaneously added to an organic solvent. It is preferred that a strong base and an organic solvent are mixed and the compound (1) is added to the obtained mixture.

The reaction of step II is usually carried out under normal pressure conditions. Proceeding of the reaction can be confirmed by conventional analysis means such as gas chromatography, high-performance liquid chromatography, thin-layer chromatography, NMR, and IR.

After completion of the reaction, the compound (2) can be isolated from the mixture by means such as crystallization, filtration, distillation, and extraction. The isolated compound (2) may be further purified by conventional purification means such as rectification and column chromatography.

Examples of the compound (2) include 5-methoxy-3-(2-methoxyphenyl)-1,3,4-oxadiazolin-2-one, 5-ethoxy-3-phenyl-1,3,4-oxadiazolin-2-one, 5-methoxy-3-(4-methylphenyl)-1,3,4-oxadiazolin-2-one, 5-methoxy-3-(4-chlorophenyl)-1,3,4-oxadiazolin-2-one, 5-ethoxy-3-(2-methoxyphenyl)-1,3,4-oxadiazolin-2-one, 5-methoxy-3-(2-fluorophenyl)-1,3,4-oxadiazolin-2-one, 5-methoxy-3-(4-bromophenyl)-1,3,4-oxadiazolin-2-one, and 5-methoxy-3-(4-nitrophenyl)-1,3,4-oxadiazolin-2-one, and 5-methoxy-3-(2-methoxyphenyl)-1,3,4-oxadiazolin-2-one is preferable.

EXAMPLES

The present invention will be described in more detail by Examples as follow, but the present invention is not limited to these Examples.

Example 1

(Step I-1) Preparation of Compound (1)

In a nitrogen-substituted 100 ml flask, 2.0 g of 1-methoxycarbonyl-2-(2-methoxyphenyl)hydrazine, 7.0 g of potassium carbonate and 50 g of acetonitrile were charged, and 8.0 g of phenyl chloroformate was added dropwise at room temperature under stirring over 1 hour, and then the mixture was stirred at the same temperature for 7 hours. The inorganic salt precipitated from the obtained reaction mixture was filtered and then acetonitrile was distilled off. When 5 g of ethyl acetate and 10 g of n-hexane were added to the residue, a crystal was precipitated. The precipitated crystal was filtered and dried to obtain 3.0 g of a pale yellow crystal.

As a result of analysis by $^1$H-NMR, the crystal was identified as 1-methoxycarbonyl-2-phenoxycarbonyl-2-(2-methoxyphenyl) hydrazine. Yield: 93%.

$^1$H-NMR (δppm, CDCl$_3$, TMS standard): 3.74 (s, 3H), 3.88 (s, 3H), 6.9-7.42 (m, 9H), 7.65 (bs, 1H)

(Step II-1) Preparation of Compound (2)

In a nitrogen-substituted 50 ml flask, 92 mg of 1-methoxycarbonyl-2-phenoxycarbonyl-2-(2-methoxyphenyl) hydrazine synthesized in step I-1 and 2 g of acetonitrile were charged and cooled to 0° C., followed by the addition of 14 mg of sodium hydride (60% in paraffin liquid) under stirring and then stirring at the same temperature for 1 hour. To the obtained reaction mixture, 10 g of ethyl acetate and 10 g of water were added and the organic layer was analyzed by gas chromatography (internal standard method). As a result, the yield of 5-methoxy-3-(2-methoxyphenyl)-1,3,4-oxadiazolin-2-one was 46%.

Example 2

(Step I-2) Preparation of Compound (1)

In a nitrogen-substituted 100 ml flask, 5.0 g of 1-methoxycarbonyl-2-(2-methoxyphenyl) hydrazine, 3.9 g of triethylamine and 15 g of tetrahydrofuran were charged and 6.0 g of phenyl chloroformate was added dropwise at room temperature under stirring over 1 hour, and then the mixture was stirred at the same temperature for 2 hours. To the obtained reaction mixture, 15 g of toluene and 15 g of a 5% hydrochloric acid solution were added and, after stirring, the mixture was allowed to stand, resulting in separation into two layers. Therefore, the aqueous layer as the lower layer was separated. In the same manner, the oil layer was washed once with 15 g of a 5% hydrochloric acid solution, washed once with 15 g of water and concentrated, and then 10 g of ethyl acetate and 20 g of n-hexane were added to the residue. As a result, a crystal was precipitated. The precipitated crystal was filtered and dried to obtain 7.7 g of a pale yellow crystal. As a result of analysis by $^1$H-NMR, the crystal was identified as 1-methoxycarbonyl-2-phenoxycarbonyl-2-(2-methoxyphenyl) hydrazine. Yield: 96%.

(Step II-2) Preparation of Compound (2)

In a nitrogen-substituted 50 ml flask, 200 mg of sodium hydride (60% in paraffin liquid) and 5 g of acetonitrile were charged and cooled to 0° C. To this mixed solution, 1 g of 1-methoxycarbonyl-2-phenoxycarbonyl-2-(2-methoxyphenyl) hydrazine synthesized in step I-2 was dividedly added (each 50 mg) at the same temperature under stirring over 30 minutes, followed by stirring at the same temperature for 30 minutes. To the obtained reaction mixture, 10 g of toluene and 10 g of water were added and the organic layer was analyzed by gas chromatography (internal standard method). As a result, the yield of 5-methoxy-3-(2-methoxyphenyl)-1,3,4-oxadiazolin-2-one was 28% and 72% of 1-methoxycarbonyl-2-(phenoxycarbonyl)-2-(2-methoxyphenyl) hydrazine as a raw material remained.

Example 3

Preparation of Compound (2)

In a nitrogen-substituted 50 ml flask, 300 g of 1-methoxycarbonyl-2-phenoxycarbonyl-2-(2-methoxyphenyl) hydrazine synthesized in Example 1 (step I-1) and 10 g of acetonitrile were charged and cooled to 0° C., followed by addition of 64 mg of a potassium hydroxide powder under stirring and then stirring at the same temperature for 1 hour. To the obtained reaction mixture, 10 g of ethyl acetate and 10 g of water were added and the organic layer was analyzed by gas chromatography (internal standard method). As a result, the yield of 5-methoxy-3-(2-methoxyphenyl)-1,3,4-oxadiazolin-2-one was 26% and 30% of 1-methoxycarbonyl-2-(phenoxycarbonyl)-2-(2-methoxyphenyl) hydrazine as a raw material was recovered.

Example 4

(Step I-3) Preparation of Compound (1)

In a nitrogen-substituted 100 ml flask, 500 mg of 1-ethoxycarbonyl-2-phenylhydrazine, 420 mg of triethylamine and 5 g of tetrahydrofuran were charged and 650 mg of phenyl chloroformate was added dropwise at room temperature under stirring for 30 minutes, and then the mixture was stirred at the same temperature for 2 hours. To the obtained reaction mixture, 10 g of toluene and 5 g of a 5% hydrochloric acid solution were added and, after stirring, the mixture was allowed to stand, resulting in separation into two layers. Therefore, the aqueous layer as the lower layer was separated. In the same manner, the oil layer was washed once with 5 g of a 5% hydrochloric acid solution, washed once with 5 g of water and concentrated, and then 3 g of ethyl acetate and 5 g of n-hexane were added to the residue. As a result, a crystal was precipitated. The precipitated crystal was filtered and dried to obtain 410 mg of a pale yellow crystal. As a result of analysis by $^1$H-NMR, the crystal was identified as 1-ethoxycarbonyl-2-phenoxycarbonyl-2-phenylhydrazin. Yield: 50%.

$^1$H-NMR (δppm, CDCl$_3$, TMS standard): 1.29 (t, 3H), 4.22 (q, 2H), 7.0-7.42 (m, 10H)

(Step II-3)

Preparation of Compound (2)

In a nitrogen-substituted 50 ml flask, 100 mg of 1-ethoxycarbonyl-2-phenoxycarbonyl-2-phenylhydrazine synthesized in step I-3 and 2 g of acetonitrile were charged and cooled to 0° C., followed by addition of 20 mg of sodium hydride (60% in paraffin liquid) under stirring and then stirring at the same temperature for 1 hour. To the obtained reaction mixture, 10 g of ethyl acetate and 10 g of water were added and the organic layer was analyzed by gas chromatography (internal standard method), and thus production of 5-ethoxy-3-phenyl-1,3,4-oxadiazolin-2-one was confirmed.

INDUSTRIAL APPLICABILITY

According to the present invention, an oxadiazolinone compound can be produced industrially easily without requiring special facilities.

The invention claimed is:
1. A compound represented by the formula (1):

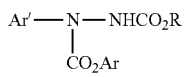
(1)

wherein Ar and Ar' each independently represents an aromatic hydrocarbon group having 6 to 20 carbon atoms which may have a substituent, and R represents an alkyl group having 1 to 4 carbon atoms.

2. The compound according to claim 1, wherein Ar is a phenyl group, and Ar' is a phenyl group which has an alkoxy group having 1 to 4 carbon atoms.

3. The compound according to claim 1, wherein Ar is a phenyl group, Ar' is a 2-methoxyphenyl group, and R is a methyl group.

4. A method for producing an oxadiazolinone compound represented by the formula (2):

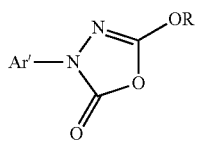
(2)

wherein Ar' and R have the same meanings as defined below, which comprises step I of reacting a compound represented by the formula (3):

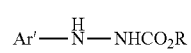
(3)

wherein Ar' represents an aromatic hydrocarbon group having 6 to 20 carbon atoms which may have a substituent, and R represents an alkyl group having 1 to 4 carbon atoms, with a compound represented by the formula (4):

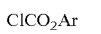
(4)

wherein Ar represents an aromatic hydrocarbon group having 6 to 20 carbon atoms which may have a substituent; and step 11 of reacting a compound represented by the formula (1):

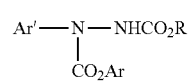
(1)

wherein Ar and Ar' each independently has the same meaning as defined above, which is obtained by step I, with a strong base.

5. A method for producing an oxadiazolinone compound represented by the formula (2):

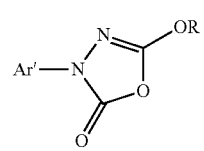
(2)

wherein Ar' and R have the same meanings as defined below, which comprises a step of reacting a compound represented by the formula (1):

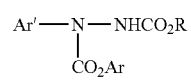
(1)

wherein Ar and Ar' each independently represent an aromatic hydrocarbon group having 6 to 20 carbon atoms which may have a substituent, and R represents an alkyl group having 1 to 4 carbon atoms, with a strong base.

6. The method according to claim 4 or 5, wherein the strong base is selected from the group consisting of an alkali metal hydride, an alkali metal amide compound, and an alkali metal hydroxide.

7. A method for producing a compound represented by the formula (1):

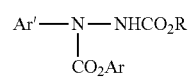
(1)

wherein Ar, Ar' and R have the same meanings as defined below, which comprises a step of reacting a compound represented by the formula (3):

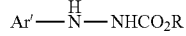   (3)

wherein Ar' represents an aromatic hydrocarbon group having 6 to 20 carbon atoms which may have a substituent, and R represents an alkyl group having 1 to 4 carbon atoms, with a compound represented by the formula (4):

$ClCO_2Ar$   (4)

wherein Ar represents an aromatic hydrocarbon group having 6 to 20 carbon atoms which may have a substituent.

8. The method according to claim 4, 5 or 7, wherein Ar is a phenyl group, and Ar' is a phenyl group which has an alkoxy group having 1 to 4 carbon atoms.

9. The method according to claim 4, 5 or 7, wherein Ar is a phenyl group, Ar' is a 2-methoxyphenyl group, and R is a methyl group.

* * * * *